United States Patent [19]

Halloran et al.

[11] Patent Number: 5,162,479
[45] Date of Patent: Nov. 10, 1992

[54] SILOXANES USEFUL IN PERMANENT WAVING OF HAIR

[75] Inventors: Daniel J. Halloran; Thomas H. Lane; Robert A. Ekeland, all of Midland County, Mich.

[73] Assignee: Dow Corning Corporation, Midland, Mich.

[21] Appl. No.: 682,490

[22] Filed: Apr. 8, 1991

Related U.S. Application Data

[62] Division of Ser. No. 596,131, Oct. 11, 1990, Pat. No. 5,061,482, which is a division of Ser. No. 442,882, Nov. 29, 1989, Pat. No. 5,045,310.

[51] Int. Cl.$^5$ .............................................. C08G 77/06
[52] U.S. Cl. ....................................... 528/17; 528/42; 528/43; 528/40; 528/34; 528/37
[58] Field of Search ....................... 528/42, 43, 40, 17, 528/34, 37

[56] References Cited

U.S. PATENT DOCUMENTS

| | | | |
|---|---|---|---|
| 4,247,674 | 1/1981 | Koshar et al. | 528/21 |
| 4,448,927 | 5/1984 | Falender et al. | 524/860 |
| 4,742,092 | 5/1988 | Inoue et al. | 528/17 |
| 4,888,405 | 12/1989 | Gamon et al. | 528/23 |
| 5,053,473 | 10/1991 | Suzuki et al. | 528/29 |

Primary Examiner—John C. Bleutge
Assistant Examiner—Margaret W. Glass
Attorney, Agent, or Firm—Sharon K. Severance

[57] ABSTRACT

The use of siloxanes for conditioning of hair is disclosed. They hold particular usefulness as substitutes for oxidizing agents in the hair waving process. A novel polymeric composition which comprises a silanol endblocked polydiorganosiloxane, cyclic siloxanes, a chlorobenzyl-functional siloxane and a catalyst is also disclosed.

3 Claims, No Drawings

SILOXANES USEFUL IN PERMANENT WAVING OF HAIR

This is a divisional of copending application(s) Ser. No. 07/596,131 filed on Oct. 11, 1990 which is a divisional of copending application Ser. No. 07/442,882 filed on Nov. 29, 1989, now U.S. Pat. Nos. 5,061,482 and 5,045,310, respectively.

This invention pertains to siloxanes that are useful as conditioning agents in permanent waving of hair. The siloxanes of this invention may be applied in place of the peroxide rinse in the typical perming process.

BACKGROUND OF THE INVENTION

Hair is comprised of structural proteins known as keratin. In the process of permanent waving of hair, keratin disulfide (KSSK) bonds are broken by the addition of a reducing agent to the hair. The hair is then curled and a oxidizing agent rinse is used to form new cross-linked (curled) KSSK bonds. Thioglycolates are the typical reducing agent used in the art which break the KSSK bonds and allow the formation of thiol groups (KSH) on the hair strands upon the addition of water. Hydrogen Peroxide is the typical oxidizing agent used in the restoration of the keratin disulfide bonds. It is usually desirable to apply these compounds to the hair from aqueous or occasionally a solvent media.

The use of peroxides in the perming process can result in damaged hair or remove non-natural color from hair. The peroxides used in perming are generally used to impart the following reaction with the hair.

$$2K-S-H + H_2O_2 \rightarrow K-S-S-K + 2H_2O \qquad (I)$$

However if two K—S—H groups are not present for the reaction, (I), to take place it is theorized that the following reaction takes place which results in damaged hair.

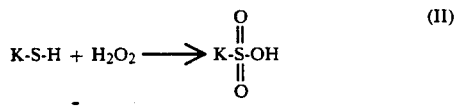
(II)

The use of certain silicones in the perming process are known in the art. For example, U.S. Pat. No. 4,331,167 to Wajaroff teaches a composition that is applied to the hair prior to the perming process which comprises a methypolysiloxane, a paraffin or isoparaffin, at least one cation active, non-capillary active compound and at least one ampholytic, capillary active imidazoline compound. This composition, when applied, allows for the retention of natural luster and oils as well as easing the process of combing, dividing and winding the hair onto the permanent wave rollers.

U.S. Pat. No. 3,687,606 to Simmler et al. teaches the use of epoxy-organo-silanes in the hair perming process. These silanes are applied after the hair has been curled, the reducing agent applied and thereafter rinsed with water but, prior to the application of the oxidizing agent. The use of the epoxy-organo-silanes during the perming process allows for better retention of curl in the hair. The problem with this method is that the perming process now requires three treatment steps which greatly lengthens the time to complete the perming process and the epoxy-organo-silanes are not water soluble.

U.S. Pat. No. 4,770,873 to Wolfram et al. teaches a neutralizing composition for hair waving and straightening comprised of a typical neutralizing (oxidizing) agent and an additive consisting of a silicone polymer (preferably in an emulsified state). The use of the silicone additive in the neutralizing (oxidizing) compound imparts durable conditioning benefits to the hair as well as reducing the water retention of the hair.

U.S. Pat. No. 4,798,722 to Edman et al. teaches a reducing solution containing additives comprised of a strong hydrogen bonding amino acids and a water soluble or emulsifiable silicone-based compound. Improvements in curl retention, manageability, feel and appearance are provided by a synergistic effect of the amino acid and the silicone.

Prior art lacks the teaching of silicone compounds that are used directly in place of the reducing or oxidizing agents. The improvements imparted by known silicones are brought about by applying them as additives blended into the reducing or oxidizing agents or by applying them independently as additional steps in the perming process.

There is also a lack of teaching of silicone compounds that are bonded directly into the hair structure. Perming processes known in the art teach methods in which the hair is oxidized back into its natural keratin disulfide (KSSK) bonds.

The novelty of this invention arises from the use of silicone compounds that are applied in place of the peroxide (oxidizing) solution. This, thereby, allows the incorporation of silicone into the hair structure.

Several chlorobenzyl functional siloxanes and methods for their preparation are known in the art. For example U.S. Pat. No. 3,925,434 to Chuang teaches an improved method for making chlorobenzyl functional chlorosilanes via the reaction of vinylbenzyl chloride with a chlorosilane.

Also, U.S. Pat. No. 3,413,329 to Pepe et al. teaches chloromethylated aralkyl silanes, alkoxysilanes and siloxanes that are useful in applications including lubricants, hydraulic fluids, coating resins for metals and fibers, and elastomers. Applications for use in hair treatment is not disclosed.

It is an object of this invention to show the use of siloxanes in the perming process.

It is also an object of this invention to show the added benefits obtained from using a siloxane in place of the peroxide rinse in the hair perming process.

THE INVENTION

This invention pertains to the use of siloxanes which contain electrophilic functionality, in particular those that contain the chlorobenzyl group, that are used in place of peroxides in the hair perming process. Siloxanes applicable in this invention are selected from the group consisting of the general formulas

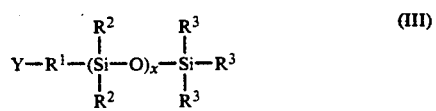
(III)

and

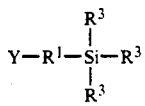
(IV)

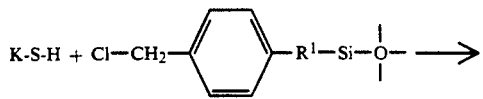
(V)

wherein $R^1$ is independently selected from alkylene groups containing 1 to 10 carbon atoms, arylene groups containing 6 to 10 carbon atoms, and alkarylene groups containing 6 to 15 carbon atoms; any of said groups optionally containing an ether oxygen within the aliphatic segments thereof; Y is selected from functionality providing an electrophilic center; $R^2$ is independently selected from an alkyl group containing 1 to 6 carbon atoms and an aryl group containing 6 to 10 carbon atoms; $R^3$ is independently selected from the group $R^2$ and the groups $-O-R^2$ and $-R^1-Y$ where $R^1$, $R^2$ and Y are as defined above; and x has the value of 1 to 5.

$R^1$ is further exemplified by ethylene, propylene, isobutylene, phenylene, ethylphenylene, glycidoxy, and others. $R^2$ is further exemplified by methyl, ethyl, phenyl, and others. Y is further exemplified by groups such as halobenzyl, epoxy, and others with chlorobenzyl being the preferred functionality. When x is 1 or greater it is preferable that at least one $R^3$ group be represented by $-R^1-Y$ and the remainder of said $R^3$ groups be selected from $R^2$.

The siloxanes useful in this invention are further exemplified by those that possess electrophilic functionality, have a low molecular weight and are compatible with aqueous or solvent delivery systems. Compounds containing at least electrophilic bifunctionality are preferred. However, compounds initially present in the perming solution may only contain mono-functionality and may react prior to or during the application process to produce at least bi-functionality.

The need for the low molecular weight is necessary for the molecule to be able to diffuse in and out of hair at a reasonable rate. Molecular weights of less than 800 and more preferably less than 400 are applicable to achieve sufficient diffusion in conventional aqueous hair care systems.

The compounds of this invention must be compatible with aqueous or solvent delivery systems so that the silicones can be easily and evenly applied to the hair after it has been wound on the curling rods. This is not a requirement of the materials and can be avoided if the compounds can be blended with low viscosity fluids that allow saturation of the chlorobenzyl compounds into the hair. Solvent and aqueous delivery systems are preferred because of cost and ease of handling.

The process for applying these materials consists of following normal perming procedures. The hair is washed and set on permanent waving curlers. The thioglycolate reducing solution or lotion is applied. The hair is allowed to set until the desired curl is achieved at which time excess thioglycolate solution is water washed from the hair. The siloxane is applied from a solution and allowed to set for a brief period of time. The hair is then water washed and styling completed as desired.

It is believed that the following reaction occurs on the hair structure during the neutralization process using, for example, a chlorobenzyl-functional siloxane where $R^1$ is as described above. This allows the incorporation of the silicone into the structure of the hair providing more durable conditioning effect. It is also believed that the K—S—C— bond provided by the materials of this invention are stronger than the K—S—S— bonds provided in typical perms thereby leading to longer lasting effects of the perm (permanent conditioning).

The siloxane neutralizer can be applied in the form of solvent or other solutions. Depending on the nature of the compound (i.e. monomeric, polymeric, number and type of functional groups etc.) will determine the proper system for delivery. Polar solvents, in particular acetone and absolute ethanol, have been found effective for compounds of the formula (III). For compounds of the formula (IV) application can be achieved by the use of non-polar solvents, silicone delivery systems, propellants, low molecular weight alkanes, isoparaffins and others. The siloxanes useful in this invention do not appear to be readily soluble in water. It may, however, be feasible to produce emulsions from the materials of the formula (III).

When applying the siloxanes of this invention from a solvent system it is desirable to add the siloxane to the solvent such that the siloxane comprises 0.1 to 50 percent (weight) of the total solution.

It is preferable that the compositions of this invention be applied from a weakly basic solution (pH approximately 8 to 9) or that the hair can be briefly treated with a weakly basic solution prior to the application of the siloxane solutions. Basic materials such as triethanolamine are useful for direct application to the hair or for addition into the siloxane solutions. The basic materials are blended into the siloxane solutions in quantities sufficient to produce the desired pH. If the basic material is applied directly to the hair, prior to the application of the chlorobenzyl solutions, it should be applied from aqueous or solvent media at concentrations sufficient to produce the desired pH.

Additional materials that are inert to the siloxanes and soluble in the chosen delivery media may be added into the oxidizing solution. These compounds may include active ingredients that impart other desirable characteristics into the hair or inactive compounds such a perfumes that improve the aesthetics of the solution.

A novel polymeric composition of this invention which has also been found useful as an oxidizing and conditioning agent for hair comprises the reaction product of a silanol endblocked polydiorganosiloxane fluid, a chlorobenzyl functional silane, low molecular weight cyclic siloxanes and a catalyst.

The silanol endblocked fluids useful in this invention may be further exemplified by the general formula

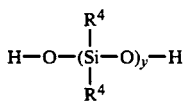

(VI)

wherein $R^4$ is independently selected from an alkyl group consisting of 1 to 6 carbon atoms and an aryl group consisting on 6 to 10 carbon atoms; and y has the value of 1 to 10,000. The preferable silanol fluids of this invention are when $R^4$ is methyl and y has the value of 10 to 1,000. The silanol fluids applicable in this invention are commercially available or can be prepared from known methods.

The chlorobenzyl functional silanes may be further exemplified by those of formula (IV) and where at least two of the $R^3$ groups is represented by the alkoxy group (-O-$R^2$), preferably methoxy. When only two of the $R^3$ groups are represented by an alkoxy group it is preferable that the remaining $R^3$ be chosen from $R^2$. The compound chlorobenzylethyltrimethoxysilane is the preferred compound.

The cyclic siloxanes useful in this composition can be further exemplified by the general formula

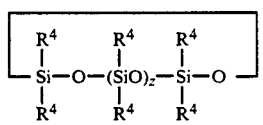

(VII)

wherein $R^4$ is as described above and z has the value of 1 to 4. Mixtures of cyclics containing varying z values are also useful in this invention. The cyclic siloxanes useful in this invention are commercially available or can be prepared from known methods.

The catalysts useful may be further exemplified by those catalysts which are capable of cross-linking a mixture of the above mentioned components. Resulting from catalysis of the cross-linking reaction are the novel polymer compositions. Organotin or orgaontitanium catalysts which contain alkyl, aryl or alkoxy groups on the tin/titanium are the preferred catalysts. The most preferred catalysts are tetrabutyl titanate or dibutyltindilaurate. Catalysts which are known for producing RTV silicone rubbers or elastomers may also be useful in this invention.

The novel polymeric composition is prepared by combining, and thereby reacting, the components described above. It is sometimes preferable to blend several of the components together prior to adding in the catalyst. One such method is to combine the silanol endblocked fluid and some of the cyclic siloxanes as one solution and the chlorobenzyl functional siloxane, the catalyst and remaining cyclics as another. The reaction is initiated at room temperature and pressure when the two solutions are combined and continues during the use.

It is desirable that the reaction mixture be comprised of 2 to 40 weight percent of the silanol endblocked fluid, 0.1 to 20 weight percent of the chlorobenzyl functional siloxane, and 0.01 to 5 weight percent of the catalyst. The remainder of the solution should comprise the cyclic siloxanes.

When the components are combined in the presence of the catalyst a reaction takes place that produces a novel polymeric composition that has a combination of di-, tri- and tetra-functional silanes and tin/titanium as well as —OH and alkoxy endblock groups.

The chlorobenzyl functionality is also present which can then be reacted with the hair in the same manner as the other siloxanes (formulas (III) and (IV)) discussed previously in this application. For hair application purposes it is preferable to dilute the polymeric composition in additional cyclic siloxanes or other suitable solvent systems such that the polymer comprises 0.1 to 50 percent (weight) of the solution.

The advantages obtained from using the compounds of this invention as neutralizers in the perming process include a durable permanent conditioning effect, softness of feel and a longer lasting wave due to the more durable chemical cross-link produced. Also, because of the bonding in the hair structure provided by the silicone, there is less potential for reversion of the bonds to free mercaptan thereby providing lower odor.

Because no peroxides are used in the process, hair that has been dyed or colored can be permed without loss or change to that color or the hair can be permed and colored simultaneously. Perming without peroxides also produces a bona-fide low damage perm.

Also, because of the bonding in the hair structure provided by the silicone, there is less potential for reversion of the bonds to free mercaptan thereby providing lower odor.

So that those skilled in the art can understand and appreciate the invention taught herein, the following examples are presented, it being understood that these examples should not be used to limit the scope of this invention over the limitation found in the claims attached hereto.

EXAMPLE 1

This example shows the preparation of a novel polymeric composition which was prepared in two parts and combined.

Part 1 consisted of 53.8 grams of a silanol endblocked fluid of the formula (VI) where all $R^4$ are the methyl group and x has a value of 30 to 40 and 52.8 grams of cyclic siloxane mixture of formula (VII) where all $R^4$ are the methyl group and z varied from 1 to 4. The two components of Part 1 were combined and mixed thoroughly. This mixture had a viscosity of 10.4 centistokes.

Part 2 consisted of 2.96 grams of chlorobenzylethyltrimethoxysilane, 1.20 grams of tetrabutyl titanate and 54.3 grams of the cyclic siloxane used in part 1. The three components or Part 2 were combined and mixed thoroughly.

Parts 1 and 2 were combined in air at room temperature. The final product has a viscosity of 26.7 centistokes. A room temperature cured film produced a soft gel. A film cured at 150° C. for 1 hour produced a soft gel.

EXAMPLE 2

Two (E and F) 2 gram European Brown tresses of virgin human hair were moistened with water, wound onto standard perming rods and treated with 10 grams of an ammonium thioglycolate acid solution (pH=10). After 45 minutes the hair was rinsed while still in the rods and blotted to remove excess moisture. The following procedures were accomplished for each tress:

Tress E was saturated with a 2.2% aqueous solution of hydrogen peroxide and allowed to stand for 5 minutes.

Tress F was saturated with a 5% aqueous triethanolamine solution (pH=8-9) and held for 5 minutes. 10.4 grams of the polymer produced in example 2 was diluted in 90.0 grams of cyclomethicone (Dow Corning 344 Fluid). This dilute solution was applied to the reduced hair. The tress was placed in a 40° C. oven for 6 minutes.

Upon completion of the oxidization step, both tresses were removed from the rods, thoroughly rinsed with water, and hung to air dry for at least 24 hours. Tress F was observed to have a tight curl, tighter than that produced on tress E. Both tresses were shampooed using a blank shampoo. Tress F was observed to have a conditioned curl upon drying and the feel was judged to be very good.

What is claimed is:

1. A composition comprising the reaction product of
(i) 2 to 40 weight percent of silanol endblocked polydiorganosiloxane fluids of the general formula

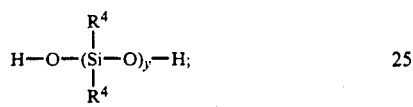

(ii) 0.1 to 20 weight percent of chlorobenzyl functional silanes of the formula

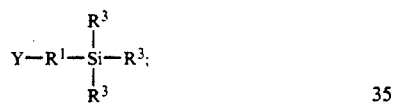

(iii) 35 to 97.89 weight percent of low molecular weight cyclic siloxanes of the general formula

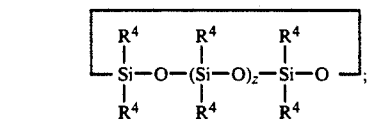

and
(iv) 0.01 to 5 weight percent of a catalyst;
wherein $R^1$ is independently selected from the group consisting of alkylene groups containing 1 to 10 carbon atoms, arylene groups containing 6 to 10 carbon atoms; and alkarylene groups containing 6 to 15 carbon atoms; any of said alkylene groups optionally containing an ether oxygen within the aliphatic segments thereof;
Y is a chlorobenzyl group;
$R^2$ is independently selected from the group consisting of an alkyl group containing 1 to 6 carbon atoms and an aryl group containing 6 to 10 carbon atoms;
$R^3$ is independently selected from the group consisting of $R^2$ and the groups $-O-R^2$ and $-R^1-Y$ with the proviso that at least two $R^3$ groups are $-O-R^2$ and where $R^1$, $R^2$ and Y are as defined above;
$R^4$ is independently selected from the group consisting of an alkyl group consisting of 1 to 6 carbon atoms and an aryl group consisting of 6 to 10 carbon atoms;
y has the value of 1 to 10,000; and
z has the value of 1 to 4.

2. A composition as claimed in claim 1 wherein the catalyst is tetrabutyl titanate.

3. A composition as claimed in claim 1 wherein y has the value of 10 to 1,000; and the silane of (ii) is a chlorobenzyl functional trimethoxy silane.

* * * * *